(12) United States Patent
Ono

(10) Patent No.: US 12,117,434 B2
(45) Date of Patent: Oct. 15, 2024

(54) OIL DETERIORATION DIAGNOSIS DEVICE

(71) Applicant: MITO KOGYO CO., LTD, Tokyo (JP)

(72) Inventor: Ichiro Ono, Tokyo (JP)

(73) Assignee: MITO KOGYO CO., LTD (JP)

( * ) Notice: Subject to any disclaimer, the term of this patent is extended or adjusted under 35 U.S.C. 154(b) by 263 days.

(21) Appl. No.: 17/789,201

(22) PCT Filed: Oct. 28, 2021

(86) PCT No.: PCT/JP2021/039761
§ 371 (c)(1),
(2) Date: Jun. 26, 2022

(87) PCT Pub. No.: WO2022/130795
PCT Pub. Date: Jun. 23, 2022

(65) Prior Publication Data
US 2023/0046877 A1 Feb. 16, 2023

(30) Foreign Application Priority Data
Dec. 15, 2020 (JP) ................................ 2020-207492

(51) Int. Cl.
*G01N 21/3577* (2014.01)
*F01M 11/10* (2006.01)
(Continued)

(52) U.S. Cl.
CPC ......... *G01N 33/2888* (2013.01); *F01M 11/10* (2013.01); *F16N 29/00* (2013.01);
(Continued)

(58) Field of Classification Search
CPC ........... G01N 33/2888; G01N 21/3577; G01N 21/59; F01M 11/10; F16N 29/00; F16N 2200/00; E02F 9/26
See application file for complete search history.

(56) References Cited

U.S. PATENT DOCUMENTS

| 5,912,179 A | 6/1999 | Alvarez et al. ................. 436/63 |
| 2017/0284068 A1 | 10/2017 | Nakamura et al. ....... E02F 9/26 |
| 2018/0003618 A1 | 1/2018 | Shinoda ............... G01N 21/251 |

FOREIGN PATENT DOCUMENTS

| DE | 102011057188 B4 * | 12/2022 | ......... G01N 21/3577 |
| JP | S62223406 A * | 10/1987 | ............. F01M 11/10 |

(Continued)

OTHER PUBLICATIONS

International Preliminary Report on Patentability (IPRP); PCTJP2021/039761, English translation; dated Jun. 13, 2023; 6 pages.
(Continued)

*Primary Examiner* — David P Porta
*Assistant Examiner* — Fani Polyzos Boosalis
(74) *Attorney, Agent, or Firm* — Fattibene and Fattibene LLC; Paul A. Fattibene

(57) ABSTRACT

Provided is an oil deterioration diagnosis device capable of detecting oil deterioration accurately and early in real time during operation of an operating machine without oil sampling. An oil deterioration diagnosis device 10 for a construction machine including an oil hydraulic circuit 1 includes: a floodlight projector 11a configured to irradiate oil flowing through the oil hydraulic circuit 1 with measuring light having a predetermined wave number or wavelength during operation of the construction machine; a photoreceiver 11b configured to receive transmitted light having penetrated the oil; a signal processing unit 11c configured to continuously or intermittently measure absorbance or transmittance; and a diagnosis unit 12 configured to detect a decrease of an antioxidant contained in the oil or an increase of a peroxide contained in the oil, based on changes in the absorbance or the transmittance.

5 Claims, 6 Drawing Sheets

(51) Int. Cl.
  *F16N 29/00* (2006.01)
  *G01N 21/59* (2006.01)
  *G01N 33/28* (2006.01)
  *E02F 9/26* (2006.01)

(52) U.S. Cl.
  CPC ......... *G01N 21/3577* (2013.01); *G01N 21/59* (2013.01); *E02F 9/26* (2013.01); *F16N 2200/00* (2013.01)

(56) References Cited

FOREIGN PATENT DOCUMENTS

| JP | H08226896 A | * | 2/1995 | | |
| JP | H08226896 | | 9/1996 | | |
| JP | H0996398 | | 4/1997 | | |
| JP | H11194124 | | 7/1999 | | |
| JP | H11511843 | | 10/1999 | | |
| JP | 2001074728 | | 3/2001 | | |
| JP | 2010181348 | | 8/2010 | | |
| JP | 2012132686 | | 7/2012 | | |
| JP | 2015141186 | | 8/2015 | | |
| JP | 2016113819 | | 6/2016 | | |
| JP | 2017120233 | | 7/2017 | | |
| JP | 2018048842 | | 3/2018 | | |
| WO | WO-2016114302 A1 | * | 7/2016 | ............ | B01D 61/00 |
| WO | WO 2016021006 | | 7/2017 | | |
| WO | WO 2016114302 | | 10/2017 | | |

OTHER PUBLICATIONS

Journal of the Japanese Society of Ship Engineering, Analysis and Explanation of Engine Oil by IR; vol. 6 No. 11, pp. 78-82; 1971.
JAST, Japanese Society of Tribologist; Kon et al, Relationship between Color of Membrane Patches and Oxidation Process of Non-Additive Mineral Oil for the Turbine; vol. 61, No. 10, pp. 59-65; 2016.
International Search Report, PCT/JP2021/039761, dated Dec. 7, 2021, 4 pages.

\* cited by examiner

I: INDUCTION STAGE
II: CHAIN INITIATION
III: OXIDE PRODUCTION RESULTING FROM PEROXIDE DECOMPOSITION
IV: INCREASE IN VISCOSITY OWING TO POLYMERIZATION REACTION

OIL DETERIORATION DIAGNOSIS DEVICE

FIELD

The present invention relates to an oil deterioration diagnosis device for operating machines including an oil hydraulic circuit.

BACKGROUND

Oil, such as lubricating oil, to be used for operating machines such as construction equipment and vehicles deteriorates through a chemical change or the like as the usage time of the oil is longer. When the oil chemically changes, the oil may lose lubricity, and such loss incurs the risk of interfering with the smooth operation of a device constituting an oil hydraulic circuit and damaging the device.

A main cause of the chemical change of oil is oil oxidization. Oil oxidization is accelerated by, for example, oxygen, humidity, moisture, metal ions, or light. In particular, oxygen in the air has the largest influence on oil oxidization. Oxygen accounting for approximately 21% of the air reacts with oil to cause an oxidation reaction.

The oil oxidation reaction occurs, in accordance with a radical chain reaction (autoxidation reaction). Specifically, a peroxide is first produced in oil. After that, the peroxide is oxidized to alcohol or ketone, and then the alcohol or the ketone becomes an oxide, such as carboxylic acid, oxy acid, or hydroxy acid. These oxides serve as secondary products to have a molecular weight increased due to ester production or the condensation polymerization of oxy acids and thereby become insoluble substances, which may cause lower lubricity.

The rate of oil oxidization is calculated in accordance with the Arrhenius' equation, K=Aexp (E/RT) [K: oxidization rate constant, R: gas constant, T: absolute temperature, E: activation energy, A: frequency factor]. The oxidization rate constant K increases as an exponential function of 1/T. It is generally considered that, when the temperature of oil increases by 10° C., a reaction rate increases twice. Furthermore, machines and equipment that use oil are prone to have higher temperature, and, in such environments, oil oxidization more easily proceeds.

Patent Literature 1 discloses that a sensor measures oil properties (temperature, density, viscosity, and dielectric constant), and determines the degree of abnormality, based on a difference between a measured value and a threshold value, and then determines whether or not an oil analysis with oil sampling needs to be conducted.

Patent Literature 2 discloses a device configured to measure a peroxide contained in lubricating oil in such manner that a part of the lubricating oil is sampled and the peroxide contained in the oil is measured using potentiometric titration or chemiluminescence.

CITATION LIST

Patent Literature

Patent Literature 1: Japanese Unexamined Patent Application Publication No. 2016-113819
Patent Literature 2: Japanese Unexamined Patent Application Publication No. 2012-132686

SUMMARY

Technical Problem

A determination method described in Patent Literature 1 is for detecting an increase in dielectric constant owing to an increase of an oxide and an increase in viscosity owing to an increase of a polymer. The determination method has a problem that an oxide is produced after a radical chain reaction proceeds to some extent, and therefore, not until oil oxidization considerably proceeds, the necessity of oil analysis can be determined.

The measurement device described in Patent Literature 2 has a problem that oil is sampled from an oil hydraulic circuit, and, using potentiometric titration or chemiluminescence, deterioration of the oil is analyzed, and hence, an operating machine under operation cannot be subject to measurement in real time without oil sampling.

As a method for analyzing oil deterioration in real time without oil sampling in an operating machine under operation, dielectric constant measurement that focuses on the polarity of an oxide can be mentioned. However, the dielectric constant of oil is influenced not only by the polarity of an oxide, but also by foreign substances (metal powder, moisture, and the likes) contained in the oil, and hence there is the risk of failing to obtain an accurate analysis result.

Therefore, a technical problem to be solved arises in order to detect oil deterioration accurately and early in real time without oil sampling during the operation of an operating machine, and an object of the present invention is to solve this problem.

Solution to Problem

To achieve the above-described object, an oil deterioration diagnosis device according to the present invention is an oil deterioration diagnosis device for an operating machine including an oil hydraulic circuit, the oil deterioration diagnosis device including: a measurement unit configured to irradiate oil flowing through the oil hydraulic circuit with measuring light during operation of the operating machine and receive transmitted light penetrating the oil to measure continuously or intermittently absorbance or transmittance; and a diagnosis unit configured to detect a decrease of an antioxidant contained in the oil when the absorbance increases or the transmittance decreases, wherein the wave number or the wavelength of the measuring light is set at a value to cause a decrease in the absorbance or an increase in the transmittance when the oil is oxidized to consume the antioxidant.

With this configuration, by detecting a decrease in the absorbance or an increase in the transmittance both resulting from consumption of the antioxidant, a decrease of the antioxidant capable of substantially preventing oil oxidization can be detected, and therefore, signs of oil deterioration can be detected in real time without oil sampling.

Furthermore, in the oil deterioration diagnosis device according to the present invention, the antioxidant is preferably a phenolic antioxidant, and the wave number of the measuring light is preferably set at 3650 to 3660 $cm^{-1}$.

With this configuration, by detecting an increase in the transmittance at a wave number of the measuring light of 3650 to 3660 $cm^{-1}$, the increase being caused by the consumption of the phenolic antioxidant contained in the oil, signs of oil deterioration can be detected in real time without oil sampling.

Furthermore, in the oil deterioration diagnosis device according to the present invention, the antioxidant is preferably zinc dialkyldithiophosphate, and the wave number of the measuring light is preferably set at 950 to 1000 $cm^{-1}$.

With this configuration, by detecting an increase in the transmittance at a wave number of the measuring light of 950 to 1000 $cm^{-1}$, the increase being caused by the consumption of zinc dialkyldithiophosphate contained in the oil, signs of oil deterioration can be detected in real time without oil sampling.

Furthermore, to achieve the above-described object, an oil deterioration diagnosis device according to the present invention is an oil deterioration diagnosis device for an operating machine including an oil hydraulic circuit, the oil deterioration diagnosis device including: a measurement unit configured to irradiate oil flowing through the oil hydraulic circuit with measuring light during operation of the operating machine and receive transmitted light penetrating the oil to measure continuously or intermittently absorbance or transmittance; and a diagnosis unit configured to detect an increase of a peroxide contained in the oil when the absorbance increases or the transmittance decreases, wherein the wave number or the wavelength of the measuring light is set at a value to cause an increase in the absorbance or a decrease in the transmittance when the oil is oxidized to produce the peroxide.

With this configuration, by detecting an increase in the absorbance or a decrease in the transmittance, the increase and the decrease being caused by the peroxide produced at the initial stage of oil deterioration, oil deterioration can be predicted in real time without oil sampling.

In the oil deterioration diagnosis device according to the present invention, the wavelength of the measuring light is preferably set at 1450 to 1480 nm or 2050 to 2100 nm.

With this configuration, when absorbance at a wavelength of the transmitted light of 1450 to 1480 nm or 2050 to 2100 nm increases with an increase of the peroxide contained in the oil, the diagnosis unit can predict oil deterioration in real time without oil sampling.

Advantageous Effects of Invention

The present invention makes it possible to detect oil deterioration accurately and early without oil sampling.

DESCRIPTION OF EMBODIMENTS

Figure 1:
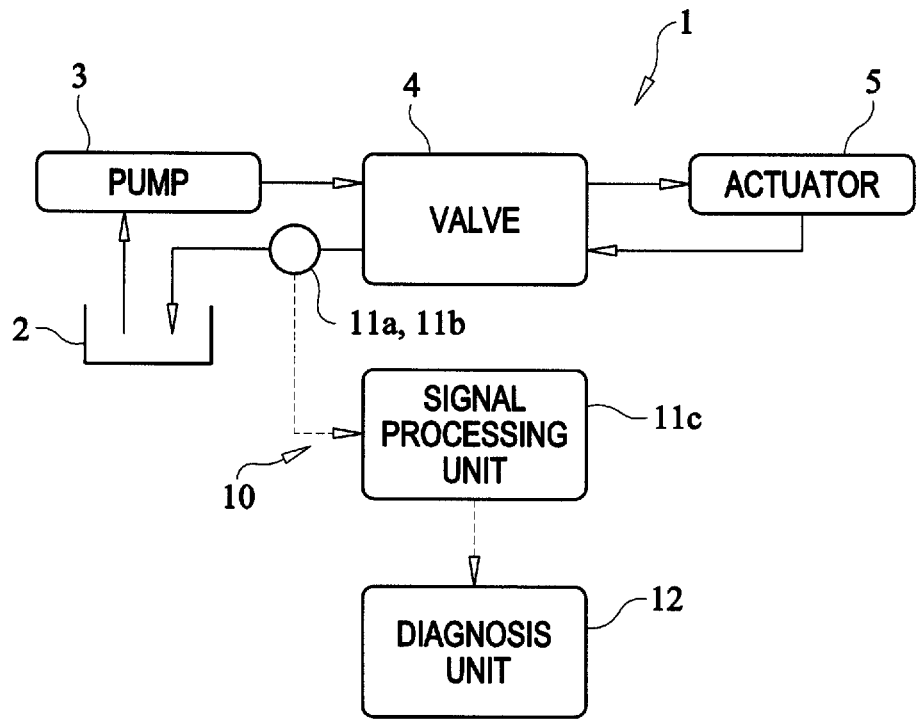
FIG. 1 is a schematic diagram illustrating a configuration of an operating machine to which an oil deterioration diagnosis device according to one embodiment of the present invention is applied.

Embodiments of the present invention will be described, based on the drawings. Note that, hereinafter, the number, numerical value, amount, range, or the like of constituents described shall not be limited to a specific number, except the case of describing them particularly clearly and the case of being theoretically clearly limited to a specific number, and these may be the specific number or larger, or the specific number or smaller.

Furthermore, the shapes and the positional relationships of constituents and the likes include what substantially approximates or is substantially similar to the shapes or the likes, except the case of particularly clearly describing the shapes and the likes and the case in which the shapes and the likes are obviously theoretically infeasible.

Furthermore, to make the feature more easily understandable, a characteristic portion is sometimes exaggerated, for example, by being magnified in the drawings. Hence, dimensions and relative size and the likes of constituents are not necessarily the same as the actual dimensions and relative size thereof. Furthermore, in the cross-sectional drawing, hatching of some constituents is sometimes omitted to make the cross-section structures of the constituents more easily understandable.

FIG. 1 is a schematic diagram illustrating a configuration of an oil-hydraulically operated construction machine to which an oil deterioration diagnosis device 10 according to one embodiment of the present invention is applied. The construction machine includes an oil hydraulic circuit 1 as a power source. The oil hydraulic circuit 1 includes an oil tank 2, an oil hydraulic pump 3, a directional control valve 4, and an actuator 5. Oil stored in the oil tank 2 is pressurized by the oil hydraulic pump 3, and supplied to the predetermined actuator 5 via the directional control valve 4. The actuator 5 is connected to a not-illustrated power source (for example, a motor or a cylinder). The oil coming back from the actuator 5 returns to the oil tank 2 via the directional control valve 4. The operation of the constituents of the oil hydraulic circuit 1 is controlled by a not-illustrated controller.

Figure 2:
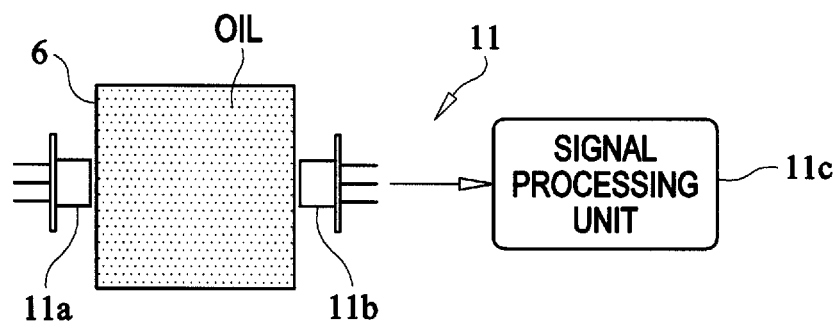
FIG. 2 is a schematic diagram illustrating a configuration of a measurement unit of the oil deterioration diagnosis device.

The oil deterioration diagnosis device 10 is configured to make a diagnosis on the degree of deterioration of the oil flowing through the oil hydraulic circuit 1. As illustrated in FIG. 2, the oil deterioration diagnosis device 10 includes a measurement unit 11 and a diagnosis unit 12.

The measurement unit 11 is an infrared sensor including: a floodlight projector 11a; a photoreceiver 11b disposed to face the floodlight projector 11a across a pipe 6 connecting the constituents of the oil hydraulic circuit 1; and a signal processing unit 11c.

The floodlight projector 11a includes a laser diode as a light source. The laser diode continuously or intermittently emits measuring light having a predetermined wave number or wavelength. The laser diode irradiates the oil flowing through the pipe 6 upstream of the oil tank 2 with the measuring light. A part of the pipe 6 is formed to be transparent so that the measuring light can penetrate the pipe 6. Note that the floodlight projector 11a may be disposed so as to irradiate the oil in the oil tank 2 with the measuring light.

The photoreceiver 11b includes: a photodiode serving as a light receiving element; and an amplifier configured to amplify a signal outputted from the photodiode. The photodiode receives the measuring light (transmitted light) having penetrated the pipe 6. The detection wavelength of the photodiode is set so as to correspond to the measuring light emitted from the laser diode.

The signal processing unit 11c is configured to calculate the absorbance or transmittance of light that the photoreceiver 11b receives. The transmittance is a ratio of the intensity of the measuring light to the intensity of the transmitted light. The absorbance is calculated from the intensity of the measuring light and the intensity of the transmitted light, based on the Lambert-Beer's law.

The diagnosis unit 12 is configured to estimate a decrease of an antioxidant or an increase of a peroxide that is contained in the oil, the decrease or the increase being caused by oil deterioration. Details of the diagnosis unit 12 will be described later.

Figure 3:
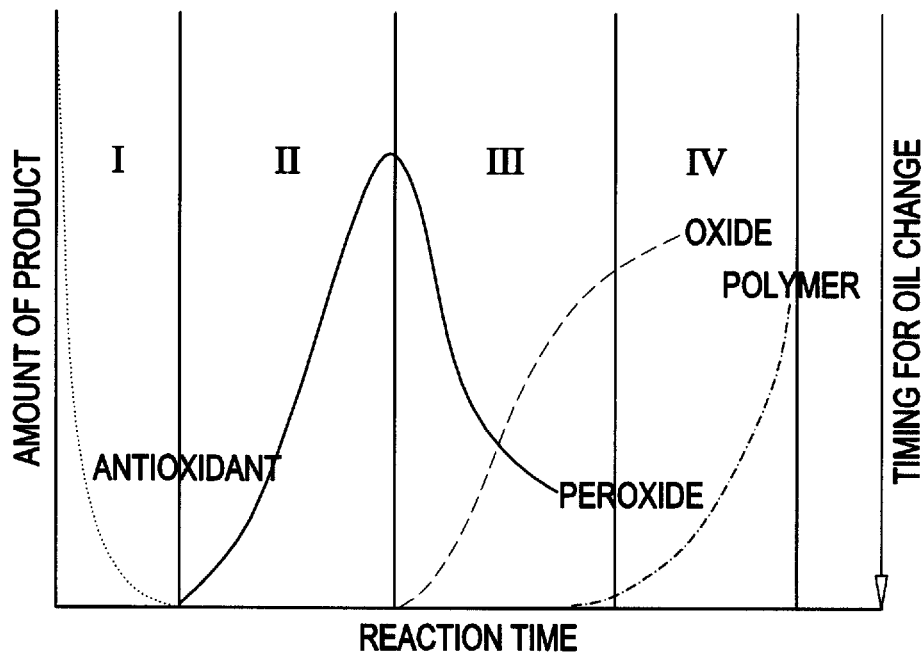
FIG. 3 is a schematic diagram illustrating a process of oil autoxidation.

Next, an oxidation reaction of oil will be described. In FIG. 3, the horizontal axis indicates the usage time of the oil, and the vertical axis indicates the amount of a product in the oil.

As illustrated in FIG. 3, first, the amount of a product in the oil varies over time in accordance with how oil deterioration is proceeding. The oil flowing through the oil hydraulic circuit 1 is prone to increase in temperature and thereby easily causes an oxidation reaction. Such oxidation reaction is caused in accordance with a radical chain reaction (autoxidation reaction). First, a peroxide exponentially rapidly increases in the oil (peroxide production stage). After that, the peroxide is oxidized to alcohol or ketone, and then the alcohol or the ketone becomes an oxide, such as carboxylic acid, oxy acid, or hydroxy acid (oxide production stage). These oxides serve as secondary products to have a molecular weight increased due to ester production or the condensation polymerization of oxy acids and thereby become insoluble substances, and as a result, the viscosity of the oil is increased to cause lower lubricity (viscosity increase stage).

A brand-new oil contains an antioxidant that reacts with a free radical to substantially inhibit a radical chain reaction. As an oxidation reaction proceeds, the antioxidant is consumed and the amount thereof decreases, and then a peroxide is produced (induction stage).

Figure 4:
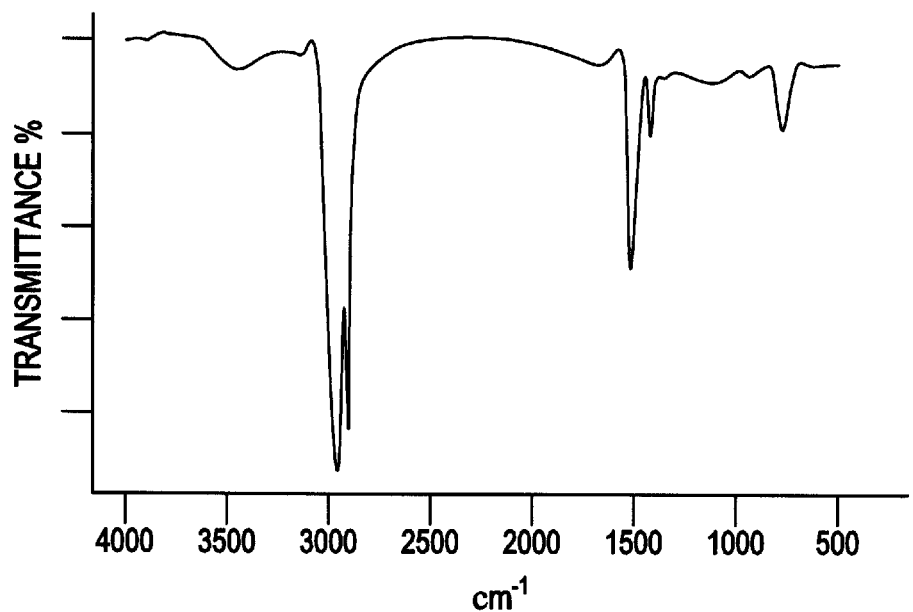
FIG. 4 is a graph illustrating an infrared absorption spectrum of common oil, the spectrum indicating a relationship between wave number and transmittance.

FIG. 4 is a graph illustrating an infrared absorption spectrum of a common brand-new oil (mineral oil). In FIG. 4, a decrease in the transmittance at a wave number of approximately 3000 $cm^{-1}$ is caused by the absorption of C—H stretching vibration, while a decrease in the transmittance at a wave number of approximately 1500 $cm^{-1}$ is caused by C—H deformation vibration. Note that when the oil is oxidized and deteriorates, the transmittance decreases at approximately 1700 $cm^{-1}$. Such decrease is caused by absorption of C=O.

Figure 5:
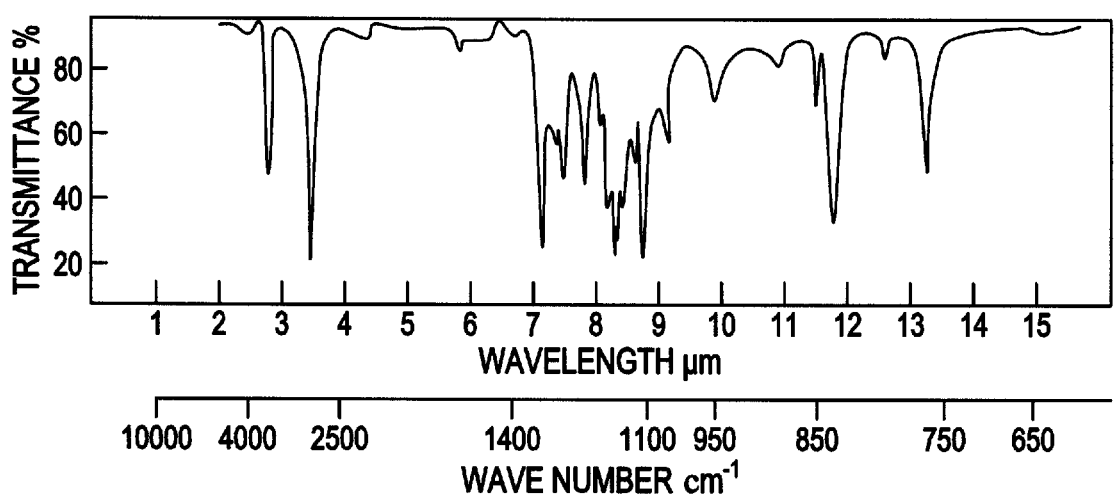
FIG. 5 is a graph illustrating an infrared absorption spectrum of oil containing an antioxidant (phenolic antioxidant), the spectrum indicating a relationship between wavelength or wave number and transmittance.
Figure 6:
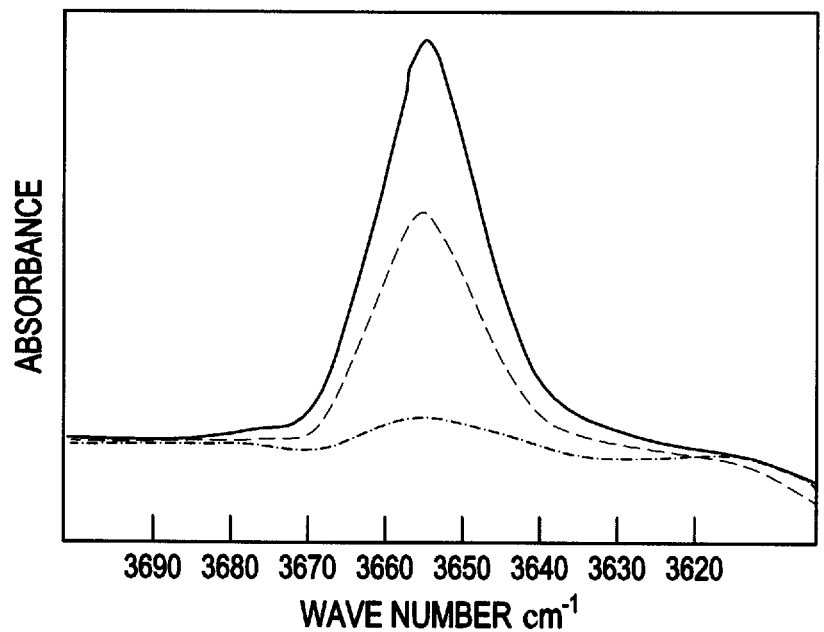
FIG. 6 is a graph illustrating an infrared absorption spectrum of oil containing an antioxidant (phenolic antioxidant), the spectrum indicating changes over time in wave number and absorbance.

FIG. 5 is a graph illustrating an infrared absorption spectrum of transmitted light in the case where the antioxidant is a phenolic antioxidant. FIG. 6 is a graph illustrating an infrared absorption spectrum indicating changes over time in absorbance at a wave number of approximately 3650 to 3660 $cm^{-1}$ in an antioxidant (phenolic antioxidant). Note that, in FIG. 6, a continuous line indicates a case of a brand-new oil, a broken line indicates a case in which oil oxidization has proceeded (the middle stage of the induction stage), and alternate long and short dash lines indicates a case in which oil oxidization has further proceeded (the final stage of the induction stage).

As illustrated in FIG. 5 and FIG. 6, transmitted light having penetrated the oil containing the phenolic antioxidant is such that, as oxidization proceeds, a decrease in the peak of absorbance, which is characteristic infrared absorption, occurs at approximately 3650 to 3660 $cm^{-1}$. In other words, it is understood that, by detecting a decrease in absorbance or an increase in transmittance at a wave number of approximately 3650 to 3660 $cm^{-1}$, a decrease of the phenolic antioxidant contained in the oil can be detected.

Figure 7:
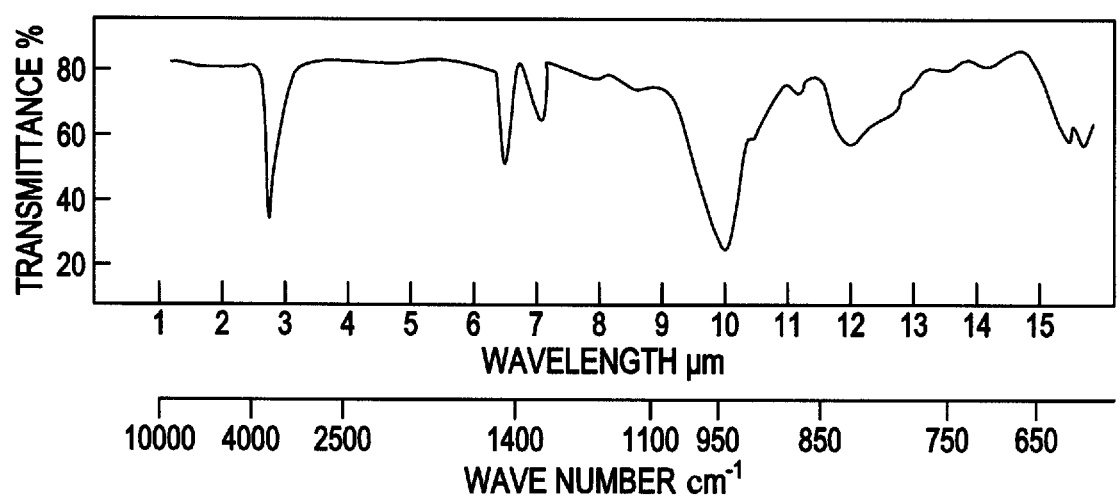
FIG. 7 is a graph illustrating an infrared absorption spectrum of oil containing an antioxidant (zinc dialkyldithiophosphate), the spectrum indicating a relationship between wavelength or wave number and transmittance.

FIG. 7 is a graph illustrating an infrared absorption spectrum of transmitted light in the case where the antioxidant is zinc dialkyldithiophosphate. As illustrated in FIG. 7, the transmitted light having penetrated zinc-dialkyldithiophosphate-containing oil is such that, when the oil is in a brand-new state, the peak of transmittance is present at approximately 1000 $cm^{-1}$, while, as oil oxidization proceeds, the peak of transmittance, which is characteristic infrared absorption, becomes higher. In other words, it is understood that, by detecting an increase in transmittance at a wave number of approximately 1000 $cm^{-1}$, a decrease of zinc dialkyldithiophosphate contained in the oil can be detected.

Figure 8:
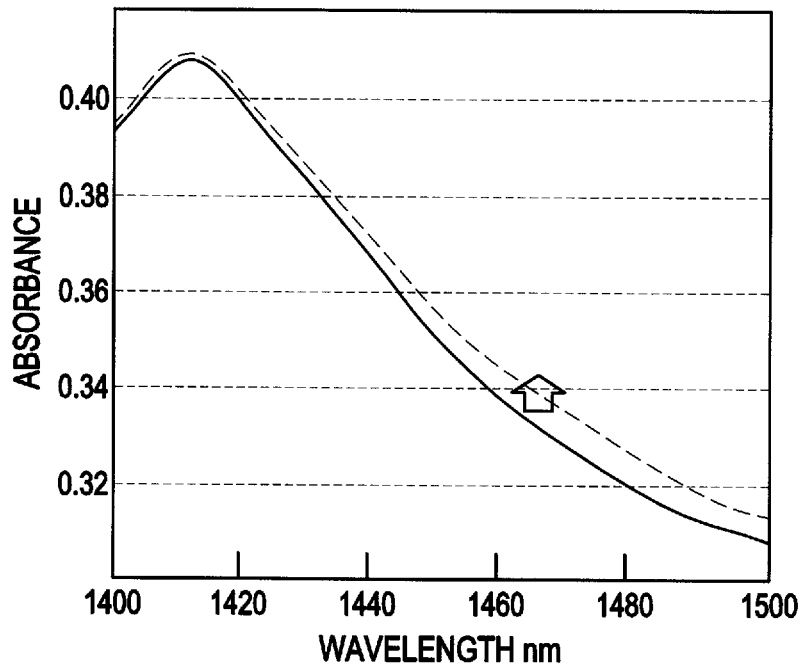
FIG. 8 is a graph illustrating an infrared absorption spectrum of oil containing a peroxide.
Figure 9:
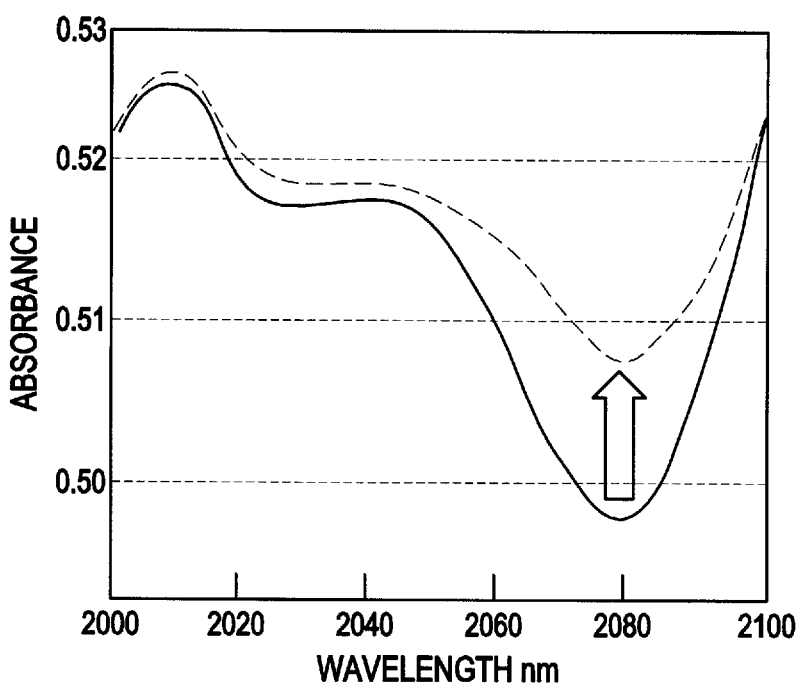
FIG. 9 is a graph illustrating an infrared absorption spectrum of oil containing a peroxide.

FIG. 8 is a graph illustrating an infrared absorption spectrum of transmitted light having penetrated an oil containing a peroxide at a wavelength of 1400 to 1500 nm. FIG. 9 is a graph illustrating an infrared absorption spectrum of transmitted light having penetrated the oil containing the peroxide at a wavelength of 2000 to 2100 nm. In FIG. 8 and FIG. 9, a continuous line indicates a case of the initial stage of the peroxide production stage (in a state in which the amount of a peroxide produced is comparatively small), and a broken line indicates a case of the final stage of the peroxide production stage (in a state in which the amount of the peroxide produced is approximately maximum).

As illustrated in FIG. 8 and FIG. 9, when an oil oxidation reaction proceeds, the peak of absorbance, which is characteristic infrared absorption, sharply increases at a wavelength of approximately 1400 to 1500 nm and a wavelength of 2000 to 2100 nm as oxidization proceeds. In other words, it is understood that, by detecting an increase in absorbance at the above-mentioned wavelengths, an increase of the peroxide can be detected.

Next, actions of the oil deterioration diagnosis device 10 will be described.

First, during operation of the construction machine, the floodlight projector 11a emits measuring light at predetermined intervals (for example, at intervals of several seconds), and the photoreceiver 11b receives transmitted light having penetrated oil flowing through the pipe 6.

The wave number or the wavelength of the measuring light is set so as to indicate a decrease in absorbance or an increase in transmittance, which is characteristic infrared absorption and caused by the consumption of the above-mentioned antioxidant. In other words, when a phenolic antioxidant is used as the antioxidant, the wave number of the measuring light is set at 3650 to 3660 $cm^{-1}$, while, when zinc dialkyldithiophosphate is used as the antioxidant, the wave number of the measuring light is set at 1000 $cm^{-1}$.

Furthermore, the wave number or the wavelength of the measuring light is set at a wavelength of 1400 to 1500 nm or 2000 to 2100 nm around which a decrease in absorbance or an increase in transmittance is indicated, the decrease and the increase being characteristic infrared absorption and caused by the increase of the above-mentioned peroxide.

The number of laser diodes disposed in the floodlight projector 11a may be one or two or more. For example, when the measurement unit 11 performs the detection of decrease of the antioxidant and the detection of increase of the peroxide, three laser diodes corresponding to the wave numbers or wavelengths indicating the decrease and the increase are provided in total. Note that both the detection of decrease of the antioxidant and the detection of increase of the peroxide are not necessarily performed, but only one thereof may be performed.

Next, the signal processing unit 11c acquires the absorbance of light received by the photoreceiver 11b. Furthermore, the signal processing unit 11c memorizes the acquired absorbance on a time-series basis so as to make a comparison in accordance with the usage time of the oil.

Next, the diagnosis unit 12 performs the detection of decrease of the antioxidant or increase of the peroxide in the oil, based on the changes over time in absorbance.

Specifically, for example, in the case where the antioxidant is a phenolic antioxidant, when absorbance decreases at a wave number of 3650 to 3660 $cm^{-1}$, the diagnosis unit 12 determines that oil deterioration has proceeded to cause consumption and decrease of the antioxidant.

Likewise, in the case where the antioxidant is zinc dialkyldithiophosphate, when absorbance decreases at a wave number of 1000 $cm^{-1}$, the diagnosis unit 12 determines that oil deterioration has proceeded to cause consumption and decrease of the antioxidant.

It may be configured such that a function indicating a relationship between the usage time of oil and decrease in absorbance at the induction stage is beforehand calculated through an experiment or the like, and, based on the function, the diagnosis unit 12 estimates remaining time of the induction stage from absorbance that the signal processing unit 11c sequentially acquires.

Furthermore, it may be configured such that the amount of time elapsed from the induction stage to the timing for oil change is beforehand calculated through an experiment or the like and memorized, and, based on the amount of time, the diagnosis unit 12 detects a decrease of the antioxidant and estimates the timing for oil change.

When the absorbance increases at a wavelength of 1400 to 1500 nm or 2000 to 2100 nm, the diagnosis unit 12 determines that oil deterioration has proceeded to cause an increase of a peroxide. In particular, a peroxide contained in oil exponentially rapidly increases at the initial stage of oil oxidization, and therefore an increase of the peroxide can be early and surely detected.

It may be configured such that a function indicating a relationship between the usage time of oil and increase in absorbance at the peroxide production stage is beforehand calculated through an experiment or the like, and, based on the function, the diagnosis unit 12 estimates remaining time of the peroxide production stage from absorbance that the signal processing unit 11c sequentially acquires.

Furthermore, it may be configured such that the amount of time elapsed from the peroxide production stage to the timing for oil change is beforehand calculated through an experiment or the like, and, based on the amount of time, the diagnosis unit 12 detects an increase of the peroxide to determine that the peroxide production stage has come, and thereby estimates the timing for oil change.

Thus, the oil deterioration diagnosis device 10 can detect how oil deterioration is proceeding in real time without oil sampling during the operation of the operating machine.

Furthermore, the oil deterioration diagnosis device 10 can simply detect oil deterioration, not by using a complicated structure, such as a spectrophotometer, that acquires a wide range of optical absorption spectra and distinguishes a substance on the basis of an absorption pattern, but by using measuring light having a predetermined wave number or the wavelength indicating characteristic infrared absorption (a change in the peak of absorbance or transmittance) corresponding to a decrease of an antioxidant or an increase of a peroxide. Furthermore, compared with the case of acquiring a wide range of optical absorption spectra, the luminous intensity of the measuring light having the predetermined wave number or wavelength can be increased with pinpoint accuracy, so that oil deterioration can be detected with sufficient accuracy.

Figure 10:
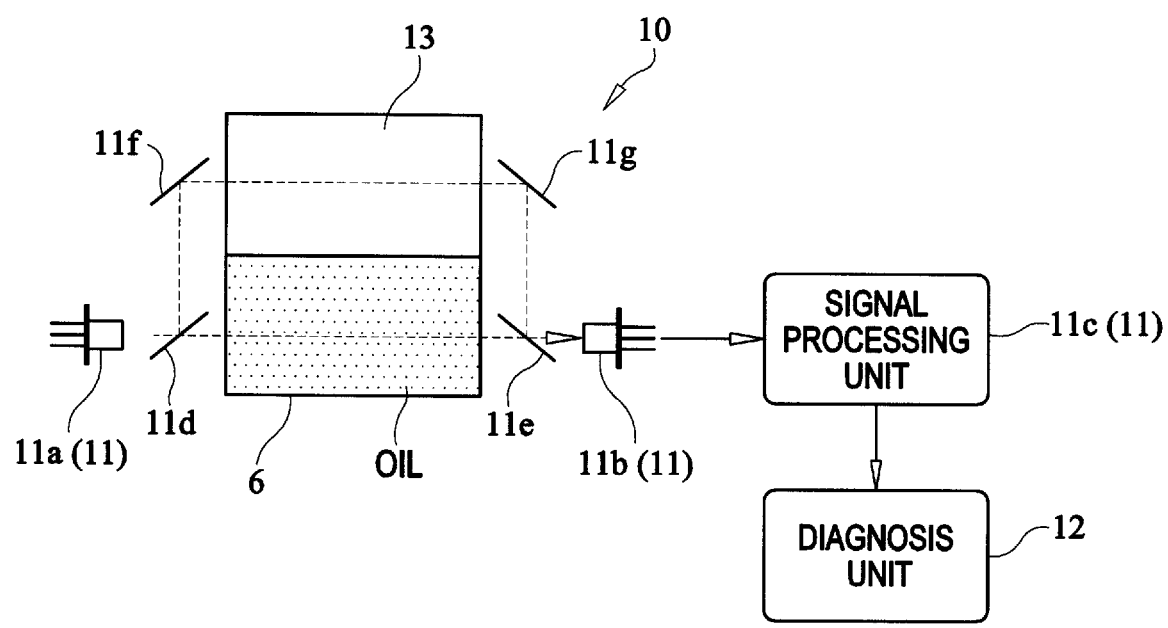
FIG. 10 is a schematic diagram illustrating an oil deterioration diagnosis device according to a modification of the present invention.

Next, a modification of the oil deterioration diagnosis device 10 will be described. As illustrated in FIG. 10, a measurement unit 11 includes a floodlight projector 11a, a photoreceiver 11b, a signal processing unit 11c, half mirrors 11d and 11e, and mirrors 11f and 11g. Furthermore, a reference container 13 filled with a brand-new oil is disposed to be adjacent to a pipe 6.

The half mirror 11d causes an optical path of measuring light emitted from the floodlight projector 11a to branch. The half mirror 11f causes reflected light reflected by the mirror 11d to refract toward the reference container 13. The mirror 11g causes reflected light having penetrated the reference container 13 to refract toward the half mirror 11e. The half mirror 11e allows transmitted light having penetrated the floodlight projector 11a to penetrate the half mirror 11e and causes transmitted light having penetrated the reference container 13 to refract toward the photoreceiver 11b.

Then, the signal processing unit 11c calculates both the absorbance of the transmitted light having penetrated the floodlight projector 11a and the absorbance of the transmitted light having penetrated the reference container 13.

Then, the diagnosis unit 12 makes a comparison between the absorbance of the transmitted light having penetrated the floodlight projector 11a and the absorbance of the transmitted light having penetrated the reference container 13, and, when the difference between the absorbances reaches a predetermined threshold, the diagnosis unit 12 can detect a decrease of the antioxidant in the oil or an increase of the peroxide in the oil in accordance with a wavelength or a wave number.

Of course, various modifications may be made to the present invention without departing from the spirit of the present invention, and the present invention also covers the modifications.

Note that a wave number is the reciprocal of a wavelength, hence a wave number can be converted into a wavelength and vice versa. Furthermore, transmittance and absorbance are correlated, hence, in the above-described embodiments, transmittance may be suitably converted into absorbance, and vice versa.

Note that an oil-hydraulically operated operating machine to which the present invention is applied is not limited to the above-described construction machine. The oil deterioration diagnosis device according to the present invention is applicable also to the diagnosis of deterioration of car engine oil and the like.

REFERENCE SIGNS LIST

1: oil hydraulic circuit
2: oil tank
3: oil hydraulic pump
4: directional control valve
5: actuator
6: pipe
10: oil deterioration diagnosis device 11: measurement unit
11a: floodlight projector
11b: photoreceiver
11c: signal processing unit
11d, 11e: half mirror
11f, 11g: mirror
12: diagnosis unit
13: reference container

The invention claimed is:

1. An oil deterioration diagnosis device for an operating machine, the operating machine including oil hydraulic circuit, the oil deterioration diagnosis device comprising:
   a measurement unit configured to irradiate an oil flowing through the oil hydraulic circuit with measuring light during operation of the operating machine and receive transmitted light penetrating the oil to measure continuously or intermittently absorbance or transmittance; and
   a diagnosis unit configured to detect changes over time in a decrease in the absorbance or an increase in the transmittance of the measuring light, and configured to estimate a time for an oil change as a function indicating a relationship between a usage time of the oil and a decrease of an antioxidant contained in the oil,
   wherein a wave number or a wavelength of the measuring light is set at a value limited to indicating characteristic infrared absorption corresponding to the decrease in the absorbance or the increase in the transmittance, when the oil is oxidized to consume the antioxidant.

2. The oil deterioration diagnosis device according to claim 1, wherein
   the antioxidant is a phenolic antioxidant, and
   the wave number of the measuring light is set at 3650 to 3660 $cm^{-1}$.

3. The oil deterioration diagnosis device according to claim 1, wherein
   the antioxidant is zinc dialkyldithiophosphate, and
   the wave number of the measuring light is set at 950 to 1000 $cm^{-1}$.

4. An oil deterioration diagnosis device for an operating machine, the operating machine including an oil hydraulic circuit, the oil deterioration diagnosis device comprising:
   a measurement unit configured to irradiate oil flowing through the oil hydraulic circuit with measuring light during operation of the operating machine and receive transmitted light penetrating the oil to measure continuously or intermittently absorbance or transmittance; and
   a diagnosis unit configured to detect changes over time in a peroxide production state wherein a peroxide contained in the oil exponentially increases resulting in an increase of the absorbance or a decrease in the transmittance of the measuring light, and configured to estimate a time for an oil change as a function indicating a relationship between a usage time of the oil and an increase of a peroxide contained in the oil,
   wherein a wave number or a wavelength of the measuring light is set at a value indicating characteristic infrared absorption corresponding to the increase in the absorbance or the decrease in the transmittance, when the oil is oxidized to consume the peroxide.

5. The oil deterioration diagnosis device according to claim 4, wherein the wavelength of the measuring light is set at 1450 to 1480 nm or 2050 to 2100 nm.

* * * * *